United States Patent [19]

Yamada et al.

[11] Patent Number: 4,760,162

[45] Date of Patent: Jul. 26, 1988

[54] INORGANIC ACID SALT OF N-(1(S)-ETHOXYCARBONYL-3-PHENYL-PROPYL)-L-ALANYLCHLORIDE AND PROCESS FOR PREPARING THE SAME

[75] Inventors: Kazuhiko Yamada, Akashi; Yoshifumi Yanagida, Takasago; Satomi Takahashi; Takehisa Ohashi, both of Kobe; Kiyoshi Watanabe, Akashi, all of Japan

[73] Assignee: Kanegafuchi Kagaku Kogyo Kabushiki Kaisha, Osaka, Japan

[21] Appl. No.: 900,050

[22] Filed: Aug. 25, 1986

[30] Foreign Application Priority Data

Aug. 27, 1985 [JP] Japan .................. 60-188242

[51] Int. Cl.$^4$ .......................... C07C 101/10
[52] U.S. Cl. ............................... 560/38
[58] Field of Search .............. 560/38; 260/544 N

[56] References Cited

U.S. PATENT DOCUMENTS

| 2,099,781 | 11/1937 | Waldron .................. 260/544 N |
| 2,126,180 | 8/1938 | Dyson et al. .............. 260/544 N |
| 4,532,342 | 7/1985 | Hoefle et al. ................ 560/38 |
| 4,556,652 | 12/1985 | Suh et al. ..................... 514/211 |
| 4,716,235 | 12/1987 | Takahashi et al. ........... 548/533 |

FOREIGN PATENT DOCUMENTS

| 0018546 | 11/1980 | European Pat. Off. . |
| 0058567 | 8/1982 | European Pat. Off. . |
| 3507576 | 9/1985 | Fed. Rep. of Germany . |
| 1241844 | 8/1971 | United Kingdom ........... 260/544 N |

OTHER PUBLICATIONS

Urbach et al, *Tetrahedron Letters*, vol. 25, No. 11, pp. 1143–1146, 1984.

Henning et al, *Chemical Abstracts*, vol. 99, No. 88067e, 1983.

Kureha Chemical Industry, *Chemical Abstracts*, vol. 100, No. 120897c, 1984.

*Chemical Abstracts*, vol. 105, No. 7, p. 649, Abstract No. 60947k, published Aug. 18, 1986.

*Primary Examiner*—Donald B. Moyer
*Assistant Examiner*—Bruce D. Gray
*Attorney, Agent, or Firm*—Armstrong, Nikaido, Marmelstein & Kubovcik

[57] ABSTRACT

An inorganic acid salt of N-[1(S)-ethyoxycarbonyl-3-phenylpropyl]-L-alanylchloride having the formula (I):

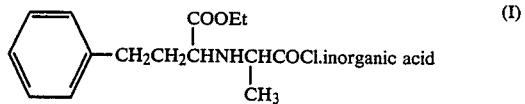

A process for preparing an inorganic acid salt of N-[1(S)-ethoxycarbonyl-3-phenylpropyl]-L-alanylchloride having the formula (I)

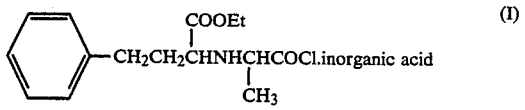

which comprises reacting an inorganic acid salt of N-[1(S)-ethoxycarbonyl-3-phenylpropyl]-L-alanine with phosphorous pentachloride in an inactive organic solvent. According to the present invention, ACEI can be economically and easily prepared.

2 Claims, No Drawings

INORGANIC ACID SALT OF N-(1(S)-ETHOXYCARBONYL-3-PHENYL-PROPYL)-L-ALANYLCHLORIDE AND PROCESS FOR PREPARING THE SAME

BACKGROUND OF THE INVENTION

The present invention relates to a novel inorganic salt of N-[1(S)-ethoxycarbonyl-3-phenylpropyl]-L-alanylchloride having the formula (I):

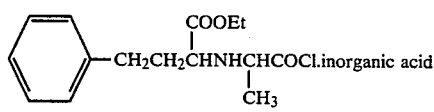

and a process for preparing the same. The inorganic salt is extremely useful as an intermediate for preparing various amino acid derivatives such as N-[1(S)-ethoxycarbonyl-3-phenylpropyl]-L-alanine derivative having the general formula (II):

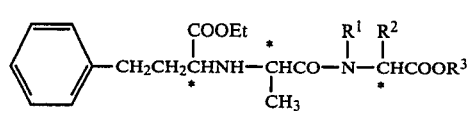

wherein $R^1$ is cycloalkyl, cycloalkylalkyl, indanyl or substituted indanyl group having 1 to 15 carbon atoms or alkoxy forms thereof; $R^2$ and $R^3$ are the same or different from each other and are hydrogen atom, a substituted or unsubstituted alkyl, aralkyl or aryl group having 1 to 7 carbon atoms; $R^1$ and $R^2$ may form a monocyclic, bicyclic or tricyclic heterocyclic ring having 1 to 15 carbon atoms together with the atoms to which they are linked; and an asterisk represents S-configuration with respect to an asymmetric carbon atom, which is expected to be an antihypertensive agent due to an excellent Angiotensin Converting Enzyme (ACE) inhibitory activity.

It is known that an Angiotensin Converting Enzyme inhibiting agent (hereinafter referred to as "ACEI") of the general formula (II), which is the final desired compound of the invention, has been prepared by, for instance, reductive amination reaction using ethyl α-oxo-γ-phenylbutyrate (IV) and a peptide containing L-alanine having the general formula (III):

wherein $R^1$, $R^2$ and $R^3$ are as defind above.

In case of enalapril or 'N-[1(S)-ethoxycarbonyl-3-phenylpropyl]-L-alanyl-L-proline which is one of the typical ACEI, it is known to be prepared by reducing a Schiff's base (VI), which is prepared by condensation reaction by dehydration between L-alanyl-L-proline (V) and ethyl α-oxo-γ-phenylbutyrate (IV), by hydrogen gas with a catalyst such as palladium/carbon or sodium cyanoborohydride (NaBH$_3$CN) [Japanese Unexamined Patent Publication No. 81845/1980 and J. Org. Chem. 49 (15), 2816 (1984)].

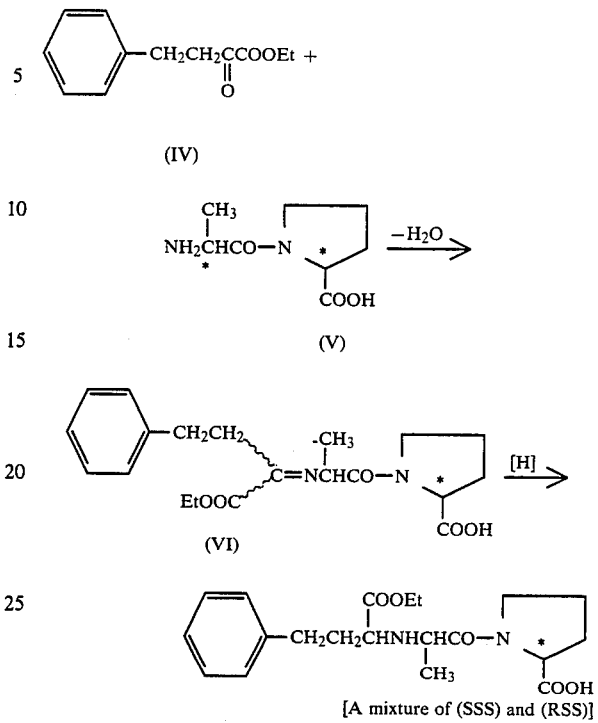

[A mixture of (SSS) and (RSS)]

On the other hand, as a method utilizing N-[1(S)-ethoxycarbonyl-3-phenylpropyl]-L-alanine, there have been known a so called active esterification method in which a base having the general formula (VII):

wherein $R^1$ and $R^2$ are as defined above, is condensed with 1-hydroxybenzotriazol (HOBt)/dicyclohexylcarbodiimide (DCC) [DCC-HOBt method] or with N-hydroxysuccinimide (HOSu)/DCC [DCC-HOSu method] (Japanese Unexamined patent Publications No. 161372/1981, No. 172367/1983 and No. 65057/1984, and the like); a so called mixed acid anhydride method in which the base (VII) is reacted with diethylcyanophosphate or phosphine acid anhydride (Japanese Unexamined Patent Publications No. 231052/1984 and No. 89497/1985, and the like).

As a general method for synthesizing a peptide bond, there have been known an azide method, a NCA method, an acid cloride method and the like, in addition to the above methods, as described in "Elements and Experiments of Peptide Synthesis" by Nobuo Izumiya. However, it has not yet been reported that ACEI (II) is synthesized by the acid chloride method using N-[1(S)-ethoxycarbonyl-3-phenylpropyl]-L-alanine.

As a general method for synthesizing acid chlorides, there has been well known a reaction of carboxylic acid with an inorganic halogen compound such as phosphoryl chloride, thionyl chloride, phosphorus pentachloride or phosphorus trichloride in an inert solvent. However, a process for preparing the object compound of the present invention, N-[1(S)-ethoxycarbonyl-3-phenylpropyl]-L-alanylchloride has not yet been reported.

ACE inhibitory activity of the various amino acid derivatives (II) is closely related to the configuration at the asymmetric carbon atom. For the desired activity, it is necessary that the derivative (II) is an optically active compound with (S)-configuration with respect to the all three asymmetric carbon atoms, i.e. (SSS) form. According to the above method for synthesizing ACEI (II) by the reductive amination reaction, however, a mixture of (SSS)-configuration and (RSS)-configuration is prepared since both (S)-configuration and (R)-configuration are produced with respect to the asymmetric carbon atom in the phenylbutyric acid part of the compound produced by the reduction of the Schiff's base having the formula (VI). Therefore, a complicated optical resolution procedure is required in order to obtain the desired compound with (SSS)-configuration, and moreover, the yield of the desired compound with (SSS)-configuration is quite low, i.e. less than 50% due to the production of a large amount of the compound with (RSS)-configuration, although each reaction proceeds in high efficiency. Therefore, starting materials which are expensive and prepared by many steps, ethyl α-oxo-γ-phenylbutyrate (IV) and L-alanyl-L-proline, may be wasted by this method. Also, in the reductive amination reaction, since the Schiff's base prepared in the reaction substantially has a tendency to undergo racemization, it has been attempted to prepare the Schiff's base in situ in the reduction system in order to avoid the racemization of the Schiff's base. However, ethyl α-oxo-γ-phenyl butyrate (IV), which is easily reduced by nature, is not only used for producing the Schiff's base but also reduced to form a by-product such as ethyl α-hydroxy-γ-phenylbutyrate, which results in a competitive wasteful consumption of the compound (IV), and thus a 2 to 3 times molar amount of the stoichiometric amount of ethyl α-oxo-γ-phenylbutyrate must be used, which leads to a disadvantage in an operation such that the complicated extraction procedure required for isolating the desired compound from the reaction mixture including a large amount of ethyl α-hydroxy-γ-phenylbutyrate by-produced.

With respect to the active esterification method utilizing N-[1(S)-ethoxycarbonyl-3-phenylpropyl]-L-alanine, it has been known that both the DCC-HOBt method and DCC-HOSu method have defects such as difficulty in removing the by-produced dicyclohexyl urea, employment of the expensive reagents in a large amount, requirement of the complicated procedure, and a yield of from only 50 to 75%. Also, serious allergy to DDC is known and thus DCC is not an industrially preferable reagent.

In the mixed acid anhydride method, a compound which is expensive and has strong toxicity, such as diethyldiaminophosphate, diphenylphosphoryl azide or alkylphosphine acid anhydride is used in order to form the mixed acid anhydride (MA) with N-[1(S)-ethoxycarbonyl-3-phenylpropyl]-L-alanine, and thus the method is not also preferable in viewpoint of economy, operability and disposal of waste fluid.

As mentioned above, the conventional method for preparing ACEI (II) is not efficient in viewpoint of economy and operability.

The present inventors previously have filed a patent application for a process for preparing economically and efficiently N-[1(S)-ethoxycarbonyl-3-oxo-3-phenylpropyl]-L-alanine and N-[1(S)-ethoxycarbonyl-3-phenylpropyl]-L-alanine, which are quite useful as the intermediate for preparing ACEI (II) (Japanese Patent Application No. 19483/1985).

The present inventors have studied in order to establish a process for preparing ACEI economically and efficiently by effectively utilizing N-[1(S)-ethoxycarbonyl-3-phenylpropyl]-L-alanine with the (SS)-configuration, which is easily prepared by the above-mentioned technique and is a common constituent of ACEI (II). As a result, it has been found that an inorganic acid salt of N-[1(S)-ethoxycarbonyl-3-phenylpropyl]-L-alanylchloride, which is one of the reactive derivatives of N-[1(S)-ethoxycarbonyl-3-phenylpropyl]-L-alanine, can be prepared almost quantitatively by the reaction between phosphorus pentachloride and an inorganic acid salt of N-[1(S)-ethoxycarbonyl-3-phenylpropyl]-L-alanine and that the obtained compound can be quite effectively utilized in the synthesis of various ACEI having the general formula (II).

SUMMARY OF THE INVENTION

According to the present invention, there is provided an inorganic acid salt of N-[1(S)-ethyoxycarbonyl-3-phenylpropyl]-L-alanylchloride having the formula (I):

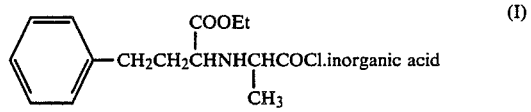

Also, according to the present invention, there is provided a process for preparing a inorganic acid salt of N-[1(S)-ethoxycarbonyl-3-phenylpropyl]-L-alanylchloride having the formula (I), which comprises reacting an inorganic acid salt of N-[1(S)-ethoxycarbonyl-3phenylpropyl]-L-alanine with phosphorous pentachloride in an inactive organic solvent.

DETAILED DESCRIPTION

The starting material used in the present invention is an inorganic acid salt such as hydrochloric acid salt or sulfuric acid salt of N-[1(S)-ethoxycarbonyl-3-phenylpropyl]-L-alanine. The solvent used in the present invention is not particularly limited insofar as the solvent is the organic solvent inactive to the reactants and the reaction product. Examples of the solvent are, for instance, hydrocarbons such as benzene, toluene, n-hexane and cyclohexane; halogenated hydrocarbons such as methylenechloride, carbon tetrachloride and trichlene; ethers such as ethyl ether, dioxane, tetrahydrofuran and dimethylsulfoxide; thioethers; carboxylic acid chloride such as acetyl chloride and benzoyl chloride; and the like. The solvent may be employed in a single form or as a mixture thereof.

In general, in the synthesis of acid chloride, an inorganic halogen compound such as phosphoryl chloride, thionyl chloride, phosphorus pentachloride or phosphorus trichloride is used as a chlorinating agent. In synthesis of the acid chloride of N-[1(S)-ethoxycarbonyl3-phenylpropyl]-L-alanine inorganic acid salt, various chlorinating agents were tried. When thionyl chloride is used, the side reaction occurs violently and the desired acid chloride is hardly prepared. A method by reacting hydrogen chloride gas with N-carboxylic anhydride (NCA) to give the acid chloride is also generally known. Although NCA of N-[1(S)-ethoxycarbonyl-3-phenylpropyl]-L-alanine prepared with phosgene was reacted with hydrogen chloride gas, the desired compound was not obtained. On the other hand, when phosphorus pentachloride is used, the inorganic acid salt of N-[1(S)-ethoxycarbonyl-3-phenylpropyl]-L-alanylchloride is almost quantitatively prepared. When phosphorus trichloride is used, although the acid chloride is not prepared from phosphorus trichloride alone, the acid chloride can be prepared when phosphorus trichloride is used in combination with chlorine gas. Accordingly, for the preparation of the desired inorganic acid salt of N-[1(S)-ethoxycarbonyl-3-phenylpropyl]-L-alanylchloride, phosphorus pentachloride or a combination of phosphorus trichloride with chlorine gas is specifically effectively employed.

The reaction easily proceeds by adding phosphorus pentachloride to a solution of the inorganic acid salt, preferably hydrochloric acid salt, of N-[1(S)-ethoxycarbonyl-3-phenylpropyl]-L-alanine in the above-mentioned solvent with stirring to prepare quantitatively the desired inorganic acid salt of N-[1(S)-ethoxycarbonyl-3-phenylpropyl]-L-alanylchloride. Although the desired acid chloride can be obtained from the starting material in a free-form, the inorganic acid salt is preferably employed in viewpoint of yield and purity. When the inorganic acid salt of N-[1(S)-ethoxycarbonyl-3-phenylpropyl]-L-alanine is used in the reaction, it is added to the above-mentioned solvent in a salt form or the free-form is suspended in the above-mentioned solvent, through which, for example, hydrogen chloride gas is passed through to give the salt.

The molar ratio of phosphorus pentachloride is not less than the equimolar amount, preferably from about 1.1 to about 1.5 times molar amount, based on the inorganic acid salt of N-[1(S)-ethoxycarbonyl-3-phenylpropyl]-L-alanine, and it use is not necessary to use in large excess. It is desirable that the reaction is carried out at low temperature, preferably at a temperature of not more than 30° C., and more preferably at not more than 10° C. in viewpoint of yield and purity. Although the isolating method of the obtained product varies with the used solvent, the product can be easily isolated in a usual manner. For example, when the inorganic acid salt of N-[1(S)-ethoxycarbonyl-3-phenylpropyl]-L-alanylchloride is insoluble and suspended in the solvent, a simple solid-liquid separating method such as filtration, centrifugation or decantation can be applied. When the salt is dissolved in the solvent, separation can be carried out by deposition by concentrating or cooling the reaction mixture.

The inorganic acid salt of N-[1(S)-ethoxycarbonyl-3-phenylpropyl]-L-alanylchloride obtained by the above-mentioned method can be used in the synthesis of ACEI efficiently without requiring an optical resolution procedure as will be shown in the following Reference Examples. For instance, the inorganic acid salt of the present invention is almost quantitatively reacted with a sodium salt of L-proline in a mixed solvent of methylene chloride and ethanol in the presence of a base such as triethylamine to efficiently produce N-[1(S)-ethoxycarbonyl-3-phenylpropyl]-L-alanyl-L-proline, which is one of the ACEI of the general formula (II). Thus, it is apparent that the inorganic acid salt of N-[1(S)-ethoxycarbonyl-3-phenylpropyl]-L-alanylchloride of the present invention is an effective and economical reactive derivative for the synthesis of ACEI.

As aforementioned, according to the present invention, the inorganic acid salt of N-[1(S)-ethoxycarbonyl-3-phenylpropyl]-L-alanylchloride, which is a common reactive derivative for synthesizing the various ACEI (II) which are expected to be useful as antihypertensive agents, can be obtained in a high yield, in a high purity and at a low price. The present invention thus provides an extremely useful process for the economical and efficient industrial production of ACEI.

The present invention is more particularly described and explained by the following Examples and Reference Examples. It is to be understood, however, that the present invention is not limited to these Examples and Reference Examples, and various changes and modifications may be made without departing from the scope of the present invention.

In the Examples, the purity of the obtained inorganic acid salt of N-[1(S)-ethoxycarbonyl-3-phenylpropyl]-L-alanylchloride was measured by reacting the obtained acid chloride with ethanol in the presence of a base to produce N-[1(S)-ethoxycarbonyl-3-phenylpropyl]-L-alanine ethylester, which was then subjected to a high performance liquid chromatography (hereinafter referred to as "HPLC"). More particularly, about 100 mg of the sample of the acid chloride was put in a 10 ml messflask, to which absolute ethanol containing 0.3% (w/v) of triethylamine was added to give 10 ml of the solution and the esterification was carried out by stirring the solution with a magnetic stirrer at room temperature for 30 minutes. To 1.0 ml of the sample of the thus obtained solution, 4 ml of ethanol solution containing 10 mg of n-propylbenzoic acid (internal standard reagent) was added, the mixture was subjected to the analysis by the column chromatography under the following conditions.

Column: Finepack SIL $C_{18}$ (made by Japan Spectroscopic Co., Ltd.) 4.6 mm ID×250 mm.

Mobile phase: 100 mM phosphate buffer (pH 7.0)/methanol=40/60 (v/v).

Flow rate: 1.0 ml/min.

Detection: 210 nm.

EXAMPLE 1

5.0 g of N-[1(S)-ethoxycarbonyl-3-phenylpropyl]-L-alanine was suspended in 25 ml of dry dichloromethane, through which hydrogen chloride gas was passed with stirring to give a solution of hydrochloric acid salt. The obtained solution was cooled to 0° C., to which 4.5 g of phosphorous pentachloride was added for 2 to 3 minutes and the mixture was stirred for 5 hours. Then white crystals deposited by distilling away the solvent from the reaction mixture under reduced pressure were washed with about 100 ml of dry ether and dried under reduced pressure to give 5.8 g of hydrochloric acid salt of N-[1(S)-ethoxycarbonyl-3-phenylpropyl]-L-alanylchloride (purity: 98%).

IR (cm$^{-1}$): 2950, 1745, 1538 and 1210.

$^1$H NMR (CDCl$_3$,δ): 7.1 to 7.3 (s, 5H), 3.8 to 4.6 (m, 4H) 2.65 to 3.0 (m, 2H), 2.3 to 2.65 (m, 2H), 1.9 (d, 3H) and 1.3 (t, 3H).

$[\alpha]_D^{25} = +40.0(C=1, CH_2Cl_2)$.

mp: 83° to 85° C. (decomposition).

EXAMPLE 2

7.0 g of hydrochloric acid salt of N-[1(S)-ethoxycarbonyl-3-phenylpropyl]-L-alanine was dissolved in 25 ml of dry dichloromethane. The mixture was cooled to 5° to 10° C., to which 5.5 g of phosphorus pentachloride was added for 2 to 3 minutes. After addition, the mixture was stirred at 5° to 10° C. for about 3 hours. Then, the reaction mixture was treated in the same manner as in Example 1 to give 7.3 g of hydrochloric acid salt of N-[1(S)-ethoxycarbonyl-3-phenylpropyl]-L-alanylchloride (purity: 98%).

EXAMPLE 3

4.5 g of N-[1(S)-ethoxycarbonyl-3-phenylpropyl]-L-alanine was suspended in 25 ml of dry dichloromethane, to which 1.5 ml of phosphorus trichloride was added. Then, hydrogen chloride gas was passed through the mixture at 0° to 5° C. with stirring to give a solution of hydrochloric acid salt. Through the obtained solution 1.4 g of chlorine gas was passed for 2 hours while keeping the temperature at 0° to 5° C. and the stirring was further continued for 3 hours. Then the obtained reaction mixture was treated in the same manner as in Example 1 to give 5.2 g of hydrochloric acid salt of N-[1(S)-ethoxycarbonyl-3-phenylpropyl]-L-alanylchloride (purity: 94%).

REFERENCE EXAMPLE 1

There was added 3.63 ml of triethylamine to 30 ml of dry ethanol solution containing 1.78 g of sodium salt of L-proline and the mixture was cooled to −40° C. To the mixture 30 ml of dry dichloromethane suspension containing 4.43g of hydrochloric acid salt of N-[1(S)-ethoxycarbonyl-3-phenylpropyl]-L-alanylchloride (purity: 98%) was continuously added with stirring for about 6 minutes and the mixture was further stirred for 1 hour at −40° C. After completion of the reaction, HPLC proved a production of 4.56 g of N-[1(S)-ethoxycarbonyl-3-phenylpropyl]-L-alanyl-L-proline. To the reaction mixture 100 ml of ion-exchanged water was added and the organic solvent was removed by concentration under reduced pressure. pH of the obtained residue was adjusted to 4.2 with 6N hydrochloric acid. To the residue a salt was added and extracted with ethyl acetate. The obtained organic layer was washed with a saturated salt solution and dehydrated with sodium sulfate, followed by distilling away the solvent under reduced pressure to give 5.0 g of oily substance.

There was added 13 ml of acetonitrile to the obtained substance to dissolve with heating. A solution of 1.39 g of maleic acid dissolved in 13 ml of acetonitrile was added to the above solution and allowed to cool at room temperature, to which seed crystal was added to give rapidly a maleic acid salt of N-[1(S)-ethoxycarbonyl-3-phenylpropyl]-L-alanyl-L-proline as white crystals. After cooling with ice, the obtained crystals were filtered off and washed with acetonitrile and then ether to give 4.52 g of white crystals.

mp: 144.5° to 145° C.

$[\alpha]_D^{25} = -42.8$ (c=1, methanol).

$^1$H-NMR (D$_2$O,δ): 1.30 (t, 3H, J=7 Hz), 1.50 to 1.70 (m, 3H), 1.75 to 2.17 (m, 3H), 2.17 to 2.53 (m, 3H), 3.38 to 3.72 (m, 2H), 3.77 to 4.07 (m, 1H), 4.07 to 4.55 (m, 4H), 6.29 (s, 2H) and 7.12 to 7.40 (m, 5H).

IR (cm$^{-1}$): 3220, 2977, 1745, 1725, 1640, 1570, 1450, 1380, 1238, 1190, 1000, 878 and 700 (KBr disk).

What we claim is:

1. An inorganic acid salt of N-[1(S)-ethoxycarbonyl-3-phenylpropyl]-L-alanylchloride having the formula (I):

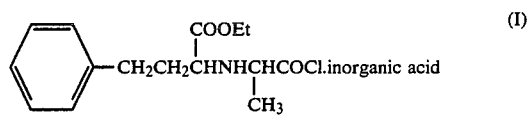

2. The inorganic acid salt of claim 1, wherein said inorganic acid salt is hydrochloric acid salt.

* * * * *